(12) United States Patent
Ryan et al.

(10) Patent No.: US 7,192,575 B2
(45) Date of Patent: Mar. 20, 2007

(54) ANTIMICROBIAL COMPOSITION

(75) Inventors: Robert Eugene Ryan, Snetterton (GB); Sandra Morris, Snetterton (GB)

(73) Assignee: Barrier Biotech Limited, Norfolk (GB)

( * ) Notice: Subject to any disclaimer, the term of this patent is extended or adjusted under 35 U.S.C. 154(b) by 390 days.

(21) Appl. No.: 10/363,270

(22) PCT Filed: Sep. 12, 2001

(86) PCT No.: PCT/GB01/04079

§ 371 (c)(1),
(2), (4) Date: Aug. 29, 2003

(87) PCT Pub. No.: WO02/21926

PCT Pub. Date: Mar. 21, 2002

(65) Prior Publication Data
US 2004/0037899 A1    Feb. 26, 2004

(30) Foreign Application Priority Data
Sep. 12, 2000  (GB) ................. 0022337.0

(51) Int. Cl.
*A61K 7/48*    (2006.01)
*A61K 9/00*    (2006.01)
*A01N 25/02*    (2006.01)

(52) U.S. Cl. ............... 424/78.02; 424/78.09; 424/405; 424/195; 424/43

(58) Field of Classification Search ......... 424/405, 424/406, 742, 45
See application file for complete search history.

(56) References Cited

U.S. PATENT DOCUMENTS 5,968,539 A    10/1999    Baier et al.
6,224,853 B1 *    5/2001    Steel et al. ............... 424/59

FOREIGN PATENT DOCUMENTS

| CH | 688 787 A | | 3/1998 |
|---|---|---|---|
| WO | WO 9927793 | * | 6/1999 |
| WO | WO 00 01423 A | | 1/2000 |

* cited by examiner

*Primary Examiner*—Johann Richter
*Assistant Examiner*—Mina Haghighatian
(74) *Attorney, Agent, or Firm*—Bacon & Thomas PLLC

(57) ABSTRACT

There is disclosed an antimicrobial composition that may be used in the treatment of diseases and conditions associated with farm animals and livestock. The composition may also be utilized as an inhibitor of microbial growth on crops, plants or foodstuffs, such as grains and the like. The composition comprises an antimicrobially effective amount of clove bud oil, eucalyptus oil, lavender oil, tea tree and orange oil but may be diluted with water prior to application.

10 Claims, No Drawings

ANTIMICROBIAL COMPOSITION

The present invention is concerned with an antimicrobial composition and, in particular, with an antimicrobial composition which is particularly useful in treating diseases and conditions associated with farm animals or livestock and which can also be utilised as an inhibitor of microbial growth on crops, plants or other foodstuffs.

There are many microbial diseases or, conditions which affect livestock of one type or another. Of particular importance are those conditions which can result or contribute to lameness or even death of an animal. Examples of such conditions include Contagious Pustular Dermatitis (Orf) in sheep, footrot in sheep and goats, in addition to foul of the foot and digital dermatitis in cattle. Orf is a virus which grows on the surface layers of the skin and in the mucous membrane of the mouth and nose. It penetrates through small abrasions in the skin. Even very minor grazes allow the virus to enter. It is a painful and disfiguring disease of sheep and goats and causes much distress to affected ewes and lambs which may result in death. Normally, when Orf occurs in individual animals, the entire flock should be treated.

Footrot is also an infectious disease of livestock including sheep, goats or cattle and it is spread from animal to animal via pasture containing bacteria from the feet of infected animals. Footrot is caused by two different bacteria—*Fusobacterium necrophorum* (found wherever sheep are found) and *Bacteroides nodosus* of which there are many different strains. Some cause a virulent form of footrot whilst others are less invasive and are termed intermediate or benign, although the latter term is misleading because it still causes considerable pain and lameness.

Digital dermatitis on the other hand occurs in cattle and is thought to be caused by the bacteria *Bacteriodes* or *Treponema* but this has not yet been completely established. Other notable conditions include sandcracks and mud fever.

Conditions of the hoof or foot of the animal are normally treated either by using antibiotics or chemical treatment baths. Orf, however, is not susceptible to antibiotics being a viral disease. A number of proprietary products claim to effect a cure, but there is no evidence to support these claims. Within a few weeks the disease can in some cases clear up on its own and all that can reasonably be done is to aim to reduce the risk of secondary bacterial infection with the use of topical antibiotic creams powders or aerosols. In serious cases antibiotics may be necessary. Vaccines are available but can only be used in flocks where the disease has occurred previously since it is an attenuated virus. Those that are available do not confer a long lasting immunity.

As regards the diseases of the hoof of the animal, foot treatments currently being used in foot baths include various chemicals such as:

(i) Formalin which is used in dilution of around 3% (1:30 parts water). However, this compound is painful to broken skin and stronger solutions can cause scald or severe cracking of skin. The product must be fresh, as it is ineffective if there is organic matter in the solution. Furthermore, it gives off toxic fumes and cannot be used indoors. It is corrosive and toxic;

(ii) zinc sulphates which are more expensive and require a lengthy stand in time of between 30–60 minutes. The product also requires a large foot bath;

(iii) organic acids normally diluted 1:50 parts water. They are generally of a very low pH and hence very acidic. They can be damagingly painful to the animal and corrosive to tissue. Organic acids are completely unselective in their treatment;

(iv) copper sulphate: this is widely used and is very toxic to sheep. It stains the fleece and is corrosive to metal and poisonous to fish.

All of the above products present serious problems of disposal and of pain for the animal. Therefore there exists a need for improved treatments for treating or alleviating many microbial diseases of livestock which are not only less expensive than those currently available but which include non-toxic ingredients which are non-painful to the animal being treated and which are safe to the environment and the user alike.

Similarly, microbial growth is a major cause of spoilage of many stored crops and of plants causing diseases including, for example, moulds and rusts and mildew. Many of these diseases are significant in horticultural systems.

Therefore, according to a first aspect of the invention there is provided an antimicrobial composition comprising an antimicrobially effective amount of clove bud oil, eucalyptus oil, lavender oil, tea tree oil and orange oil. The formulation has been found to be particularly effective in treating diseases associated with livestock/farm animals and especially those conditions such as Orf or ringworm and those affecting the foot or hoof of the animal. The composition has been found to be extremely effective in treating those diseases-caused by a viral, fungicidal or bacterial agent.

Not only has the composition been found to be useful in treating various microbial related animal diseases, but it has also been found that the composition is versatile enough in terms of its antimicrobial action to be effective against microbial diseases in plants and yet is sensitive enough so as not to kill the plants or crop. The composition is therefore particularly broad spectrum in its mode of action and can be used for treating many types of such conditions. Livestock diseases which are most notably dealt with include Contagious Pustular Dermatitis in sheep (otherwise known as Orf) scald and fibromas, footrot in sheep, cattle and goats in addition to digital dermatitis and foul of the foot in cattle. Mud fever, especially occurring in horses is also particularly infectious, and this is also advantageously dealt with by the composition of the invention. Other diseases in crops and plants which are most notably treated include mildew, mould growth, rusts, leaf spots and such like.

The formulation is, advantageously, based on a unique blend of essential oils, all of which are safe to use and which can be disposed of effectively. Neither the Council of Europe's Committee of Experts on flavouring substances nor any other European Committee has recommended limits on the use of these ingredients. Similarly, each of the ingredients has been evaluated by the US Flavouring Extract Manufacturers' Association (FEMA) who have classified them as GRAS (generally recognised as safe).

Preferably, the composition comprises approximately by volume, 16–36% clove bud oil, 34–54% eucalyptus oil, 3.5–13.5% lavender oil, 2–6% tea tree oil, and 7.5–27.5% orange oil. When the composition is for application to animals or livestock it, preferably, includes a thickening agent which allows it to adhere better to the animal. Suitable thickening agents include, for example, a gelling agent, but preferably comprises lanolin or its derivates, including lanolin oil, lanolin wax, lanolin alcohols, lanolin fatty acids, isopropyl lanolate acetylated lanolin, acetylated lanolin alcohols, lanolin alcohol linoleate, and lanolin alcohol riconoleate. In an even preferred embodiment the composition is further diluted with water. Such a composition preferably comprises a surfactant. In this aspect the composition comprises 5–15% clove bud oil, 10–23.5% eucalyptus oil, 1–6% lavender oil, 0.5–2.5% tea tree oil, 3–9.5% orange oil, 0.5–2.5% lanolin, 0.5–2.0% surfactant and 40–80% water. The composition may be even further diluted prior to application depending on the nature and severity of the condition or disease being treated.

As aforementioned the compositions according to the invention are also particularly useful in treating microbial diseases of livestock and particularly those of the foot or hoof of an animal, and particularly those conditions associated with a bacterial, viral or fungicidal agent. For treating these types of diseases the composition according to the invention, may be provided in the form of a foot bath. However, the composition may also be applied in any other suitable formulation, such as a cream or as a spray or aerosol for direct application to the infected area or area to be treated. The application of the composition to the animal in question can also confer a preventative or prophylactic effect as it can prevent secondary infection of conditions such as sandcracks or fissures which can often develop in livestock and which frequently become infected.

Providing the composition in the form of a spray as opposed to a foot bath when the composition is for application to a livestock animal offers significant advantages as the composition is applied directly to the affected area. As aforementioned, the properties of the composition are such that there is no pain or discomfort to the animal when the composition is applied either by means of a foot bath or a direct spray. In fact the composition when applied to the affected area advantageously confers a soothing affect to the animal.

The composition may be formulated with conventional propellants for dispersing as aerosols from conventional pressurised containers but preferably a non-propellant based system is used, such as a trigger pump spray bottle to produce an aerosol using the pump mechanism which builds the necessary pressure to produce the aerosol.

As is known, oil of eucalyptus is obtained from various species of eucalyptus and the resulting oils do not possess a uniform analysis. It is believed, however, that the properties of the eucalyptus oil used in the formulation according to the present invention are not dependent on a particular source of oil of eucalyptus and one may use oil derived from *Eucalyptus globulus* and/or *Eucalyptus dives*. *Eucalyptus* oil is rich in cineole and desirably *eucalyptus* oil according to the invention comprises cineole and preferably 1–8 cineole in an amount of from approximately 35 to 90% by volume.

In another aspect, there is also provided a composition according to the invention for use in controlling or alleviating microbial diseases, which in one embodiment may be associated with farm animals or livestock. Particularly preferred conditions to be treated are those associated with the hoof of ungulate animals. As aforementioned, the composition of the invention is particularly advantageous in treating bacterial, viral or fungicidal diseases or conditions, such as footrot, Orf, foul of the foot and digital dermatitis. However, it has also been surprisingly found that the composition is of broader spectrum being active against not only those diseases mentioned above and specified in the following examples, but also in treating ringworm in livestock animals such as cattle. The composition may also be adapted for internal administration to the animal for use as a wormer, for example. As aforementioned, the composition can also be used to treat for example mould in crops which are being stored, for example, in treating mildew or rust or leaf spots on plants or other similar conditions such as moulds, rusts or mildew, including white blister, powdery mildew, downy mildew, grey mould/botrytis, shothole, fungal leaf spots, blackspot, white rot or sooty mould.

Thus, in a further aspect there is provided a method for controlling or alleviating the presence of microorganisms at a locus, which method comprises applying thereto an effective amount of a composition according to the invention. Preferably, those microorganisms are present on an animal and which are responsible for any of Contagious Pustular Dermatitis (Orf), footrot, digital dermatitis, or foul of the foot, scald or ringworm in any of said ungulate animals. As aforementioned, the composition may be applied in the form of a spray or in the case of hoof associated conditions, as a foot bath as appropriate. Alternatively, the microorganisms may be present on plants or stored crops or foodstuffs causing plant diseases such as moulds, rusts or mildew, including white blister, powdery mildew, downy mildew, grey mould/botrytis, shothole, fungal leaf spots, blackspot, white rot or sooty mould.

The term "microorganism" as defined herein should be taken to mean any bacterial, virus, fungi or single cellular/unicellular or proteinaceous agent capable of transmitting disease or symptoms thereof to an animal or mammal, a plant or foodstuff.

The present invention may be more clearly understood with reference to the following examples of the invention which are provided purely by way of example only.

EXAMPLE 1

A foot bath or spray for application to affected animals was prepared in any of 200 L, 100 L or 50 L batches as desired in accordance with the following composition.

| | FUNG. FOOT SPRAY/BATH - FOR SHEEP/CATTLE 500 mls Spray 5 L bath | | |
|---|---|---|---|
| To Make | 200 L<br>40 × 5 L<br>400 × 500 mls | 100 L<br>20 × 5 L<br>200 × 500 mls | 50 L<br>10 × 5 L<br>100 × 500 mls |
| Clove Bud | 20 L | 10 L | 5 L |
| Eucalyptus | 33.5 L | 16.75 L | 8.4 L |
| Lavender | 6.5 L | 3.25 L | 1.6 L |
| Tea Tree | 3.25 L' | 1.6 L | 800 mls |
| Orange Oil | 13.5 L | 6.75 L | 3.4 L |
| Aqualose LL 100 | 3.25 L | 1.6 L | 800 mls |
| Surfacare | 2.5 L | 1.25 L | 630 mls |
| Water | 117.5 L | 58.8 L | 29.37 L |

1. Summary

On May 8, 2001 (Day 0), fifty 12 week old indoor reared Suffolk cross Mule lambs were allocated to five groups of 10 animals following foot scoring for Ovine Interdigital Dermatitis (OID). Groups were treated with Barrier Foot Bath or Barrier Foot Spray while the remaining 10 lambs were left as untreated controls. Feet were scored on Day 0, 2, 7, 9 and 14. Lambs were re-treated on Day 7. All treatments reduced the group foot score over the 14 day period compared to the untreated controls.

2. Objective

To evaluate the efficacy of two Barrier Animal Health formulations (Barrier Foot Bath and Barrier Foot Spray) in a field situation against scald (Ovine Interdigital Dermatitis or OID) in lambs against untreated controls.

3. Materials and Methods

3.1 Site Details

The sheep were located at Roundhay Farm, Yardley Hastings, Northampton and were housed throughout the trial. The building used was well ventilated and drained and lambs were stocked at approximately 1 m sq per lamb. They were bedded on dry straw. Proprietary creep pellets were fed ad lib from purpose built creep feed hoppers.

3.2 Animals

The trial was conducted on 50 Suffolk cross Mule lambs. They were born in February and had been weaned off their mothers at approximately 7 weeks of age. (This was due to movement restrictions imposed by FMD) At the start of the trial they were on average 12 weeks old and weighed in the range 30–40 Kgs. The lambs had been housed since birth and scald was identified as a problem in a significant proportion of the group prior to the start of the trial. They had not been treated for scald in the previous 14 days.

All lambs were in good health, (with the exception of lameness due to scald), throughout the trial. Each lamb was identified with an individual numbered ear tag and the groups were subsequently marked with different coloured spray marker on the neck. The lambs feet were cleaned and trimmed as necessary before scoring and subsequent treatment.

3.3 Inclusion Criteria

For inclusion in the trial, a lamb had to have at least one foot affected by scald. In addition, any lambs with feet that showed signs of physical damage or footrot were excluded from the trial.

3.4 Treatments

Lambs were tagged, their feet scored (see protocol at Appendix 1) and then randomly allocated to one of the 5 groups. Each group was then allocated to a treatment, 10 animals (40 feet) per group. Treatments were applied on May 8, 2001 (Day 0) between 1.15 pm and 2.15 pm and again on May 15, 2001 (Day 7) between 12.30 pm and 1.30 pm. On each occasion feet were cleaned with water and trimmed as necessary before treatments were applied.

| GROUP/COLOUR | TREATMENT | BATCH NUMBER |
|---|---|---|
| 1 - Green | None - untreated controls | N/A |
| 2 - Red | Barrier Foot Bath 1:200 in water | 61050701 Exp May 01, 2001 |
| 3 - Blue | Formalin 5% - Strathclyde Nutrition Formaldehyde 35%; methanol 10% | 107/1141 |
| 4 - Purple | Barrier Foot Spray | 62050701 Exp May 01, 2002 |

All treatments were applied according to the manufacturers instructions. The footbath treatments were carried out in a polythene bath containing 100 litres of water, giving an average depth of 55 mm to cover the whole foot above the coronet. Both water and product were measured accurately into the bath with calibrated containers.

3.5 Weather Conditions

The 8 May was relatively warm (15–18 Degrees centigrade) with a light breeze. There was some shade on site an the animals were not het stressed at any time. On 15 May it was cooler and there had been overnight rain.

3.6 Adverse Reactions

Observations after treatment confirmed there were no adverse reactions immediately after treatment in the Barrier Footbath, or Barrier Footspray nor were any reactions noted during the following 48 hours. However, in the 5% formalin treated group, the lambs with badly affected feet were in obvious discomfort afterwards. Several refused to put the bad foot down and take weight on it, most stood up against the wall with drooped heads and ears. This lasted for 20–30 minutes, after which there appeared to be no persistent effect.

3.7 Animals Removed from the Trial

No animals were removed from the trial. Four feet of score 4 had to be removed from the control group on Day 2 because they were deteriorating further and welfare considerations demanded treatment.

3.8 Monitoring

The feet were scored 'blind' (i.e. group unknown at time of scoring) on all occasions (Day 0, Day 2, Day 7, Day 9 and Day 14).

3.9 Other Treatments

No other treatments were given to the lambs during the course of the trial.

4. Results

For the purposes of analysis and discussion, the results have been collated in two ways:

4.1 Total Foot Scores for Each Treatment Group

Table 1 shows the total foot score by group on Day 0, 2, 7, 9 and 14. These results demonstrate that all treatments had an effect on the total foot scores of the groups.

TABLE 1

TOTAL FOOT SCORE FOR EACH GROUP

| GROUP | Day 0 | Day 2 | Day 7 | Day 9 | Day 14 |
|---|---|---|---|---|---|
| 1 - Control | 42 | 45 | 43 | 37 | 47 |
| 2 - Barrier Foot Bath | 39 | 36 | 39 | 31 | 34 |
| 3 - Formalin 5% | 40 | 35 | 47 | 27 | 31 |
| 4 - Barrier Foot Spray | 42 | 39 | 49 | 35 | 38 |

(* significant at $p <= 0.01$)

The barrier products reduced the incidence of the condition. Formalin fared only slightly better but caused significant pain to the animals.

5. Discussion and Conclusion

Therefore all treatments had a positive effect on group foot score, reducing the total score compared to the controls over the trial period.

EXAMPLE 2

Trials Commenced 1, Nov. 2000

Various grain feeds (untreated) were selected for trials which were to last for 12 weeks. We diluted the Antimicrobial Composition and sprayed the feed in exactly the same way as would have been done in their Mill. Currently AP201 ammonium propionate mould inhibitor (normally diluted 1:10) is used on many feeds. It is sprayed at the final stages using a fine mist directly to the feed as it is carried along a conveyor system for packing.

A total of eleven trials were carried out using different dilution rates varying from 1:10 to 1:200.

After we applied our composition, the feed was stored in warm and moist conditions. After 12 weeks, the samples were tested for the presence of moulds and the results are shown in Table 1. In this test 11 samples were used of the feed. 5 grams of each sample were reconstituted with 10 ml of sterile recovery medium. 1 gram of the resulting suspension was spread onto selective mould enhancing growth medium and incubated at 22° C. for 6 days. The trials had to be carried out over a twelve week period as that is the length of time feed manufacturers would like the feed to remain mould free.

Plant Protection

The same antimicrobial composition was tested on various moulds between 1, Apr. 2001 and 15, Jul. 2001. We tested the composition—diluted 20 mls in 10 L water and applied the mixture to 38 various Roses, which were suffering with Powdery Mildew. The sites were at Snetterton and Easton where we found several affected bushes and climbers.

We were very surprised at the speed in which the plants recovered. Six weeks after application, none of the plants showed signs of Mildew.

We went on to test the same product on fruit trees which included apple, pear, cherry and plum. The trees were affected with Bacterial Leaf Spots and Rusts. We removed the affected leaves and applied our formula to the point of run off to all of the green foliage. Four weeks later there was absolutely no sign of Leaf Spots or Rust returning and all of the trees went on to fruit very well.

Throughout the entire summer, many other plants including trees, shrubs, bulbous plants, vegetables and indoor plants were tested and on every occasion, the formula seemed to work very well were any type of fungi existed. It also seemed to prevent new fungi developing for around 12 weeks.

TABLE 1

| Sample | Mould c.f.u. per gram sample |
| --- | --- |
| A | <1 |
| B | <1 |
| C | <1 |
| D | <1 |
| E | <1 (1:50 dilution) |
| F | <1 |
| G | <1 |
| H | 4 (1:50 dilution) |
| J | <1 |
| K | <1 |
| L | 20 (1:200 dilution) |

The invention claimed is:

1. A composition comprising, by volume, 16–36% clove bud oil, 34–54% eucalyptus oil, 3.5–13.5% lavender oil, 2–6% tea tree oil and 17.5–27.5% orange oil wherein the volume percentages are based upon total volume of the composition.

2. A composition according to claim 1 further comprising a thickening agent.

3. A composition according to claim 2 wherein said thickening agent is lanolin.

4. A composition according to claim 3 comprising, by volume, 16–36% clove bud oil, 34–54% eucalyptus oil, 3.5–13.5% lavender oil, 2–6% tea tree oil, 17.5–27.5% orange oil and 2–6% lanolin.

5. A composition according to claim 4 which is further diluted with water.

6. An antimicrobial composition comprising, by volume, 5–15% clove bud oil, 10–23.5% eucalyptus oil, 1–6% lavender oil, 0.5 to 2.5% of tea tree oil, 3–9.5% orange oil, 0.5%–2.5% lanolin, 0.5–2.0% surfactant and 40–80% water wherein the volume percentages are based upon total volume of the composition.

7. A composition according to claim 6 wherein said lanolin is Aqualose LL100.

8. A composition according to claim 6 wherein said surfactant is polyoxyethylene which is Surfacare T20.

9. A composition according to claim 1 which is diluted further prior to application.

10. A composition according to claim 1 which is formulated for application as a spray.

* * * * *